United States Patent
Leighton et al.

[11] Patent Number: 5,884,953
[45] Date of Patent: Mar. 23, 1999

[54] GRIPPING DEVICE

[76] Inventors: Steven S. Leighton; Dawn Leighton, both of 47 Little Mill Rd., Sandown, N.H. 03873

[21] Appl. No.: 970,296

[22] Filed: Nov. 14, 1997

[51] Int. Cl.$^6$ ............................... A61B 17/50; B25B 9/02
[52] U.S. Cl. ............................................ 294/99.2; 606/210
[58] Field of Search ............................... 294/7, 8, 8.5, 11, 294/16, 25, 28, 29, 33, 99.2, 104, 106, 902; 606/131, 133, 138, 205–207, 210

[56] References Cited

U.S. PATENT DOCUMENTS

| | | | |
|---|---|---|---|
| 856,446 | 6/1907 | Collins | 294/7 |
| 1,299,299 | 4/1919 | Romer | 294/99.2 |
| 1,992,275 | 2/1935 | Zettler | 294/99.2 |
| 2,730,397 | 1/1956 | Hodska | 294/99.2 X |
| 3,861,036 | 1/1975 | Eichhorn | 294/99.2 X |
| 4,413,034 | 11/1983 | Anderson | 294/25 X |
| 4,802,704 | 2/1989 | Burns | 294/99.2 |

FOREIGN PATENT DOCUMENTS

| | | | |
|---|---|---|---|
| 8645 | 8/1905 | Denmark | 294/99.2 |
| 1231087 | 9/1960 | France | 294/99.2 |
| 675632 | 5/1939 | Germany | 294/99.2 |
| 1281256 | 1/1987 | U.S.S.R. | 606/210 |

*Primary Examiner*—Johnny D. Cherry
*Attorney, Agent, or Firm*—Bourque & Associates, P.A.

[57] ABSTRACT

A gripping device is used to grip and remove a relatively small item or particle from a larger object, such as a tick or other parasite attached to an animal or human, a fruit stem, or a sliver or splinter. The gripping device includes first and second opposing members coupled at a proximal end, for example, by an integral hinge. A gripping region is formed between the distal ends of the first and second opposing members. The first opposing member has a larger surface area and preferably a substantially circular shape adapted to be easily held by the hand of a user. The second opposing member has an arcuate shape at the distal end such that the relatively small particle is more easily disposed within the gripping region formed by the distal ends. The first and second opposing members are preferably made of one piece, for example, from a metal, plastic, or other suitable material. The distal ends on the first and second opposing members are adapted to move together when the first and second opposing members are squeezed by the user, such that the gripping region closes against the attachment. The distal ends are adapted to move apart when the first and second opposing members are released by the user.

10 Claims, 2 Drawing Sheets

GRIPPING DEVICE

FIELD OF THE INVENTION

The present invention relates to gripping devices and, more particularly, a gripping device that can easily be held by a user for removing relatively small particles or objects, such as ticks or other parasites, attached to a larger object.

BACKGROUND OF THE INVENTION

Tweezers are well known devices used to grip and remove relatively small particles attached and extending from larger objects. One common use for tweezers is to remove splinters or ticks or other parasites that have become attached to the skin of an animal or human. Existing tweezers have narrow opposing arms that are held by the user and narrow jaws that grip the small particle. The narrow arms and jaws, however, make the tweezers difficult to handle, particularly when used to remove ticks from beneath the fur of a dog or other animal. The narrow jaws must be precisely positioned around the tick or other relatively small particle that is to be gripped and removed. The narrow arms are often difficult to hold and manipulate.

Accordingly, a need exists for a gripping device that can be more easily held and maneuvered by the user. A need also exists for a gripping device that has a gripping region that can be more easily located around the tick or other relatively small particle being removed.

SUMMARY OF THE INVENTION

The present invention features a gripping device for gripping a particle, such as a tick, parasite, stem, sliver, splinter or other relatively small particles, attached to an object. The gripping device comprises first and second opposing members coupled together at a proximal end and spaced apart at a distal end of each of the first and second opposing members. The first opposing member has a larger surface area than the second opposing member for facilitating manipulation by a hand of a user.

The gripping region is disposed at the distal ends of the first and second opposing members. The distal ends of the first and second opposing are adapted to move together when the first and second opposing members are squeezed by the user such that the gripping region closes against the particle or object. The distal ends are adapted to move apart when the first and second opposing members are released by the user.

According to the preferred embodiment, the first opposing member has a substantially circular shape and is substantially flat. The second opposing member preferably includes a bend such that the distal end of the second opposing member generally faces the distal end of the first opposing member. The second opposing member also preferably includes substantially parallel edges extending from the proximal end to the distal end of the second opposing member, which has an arcuate shape.

According to the preferred embodiment, the first and second opposing members are formed as one-piece and form an integral hinge at the proximal end. The first and second opposing members can be made of a metal material that is bent to form the integral hinge at the proximal ends of the first and second opposing members.

DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
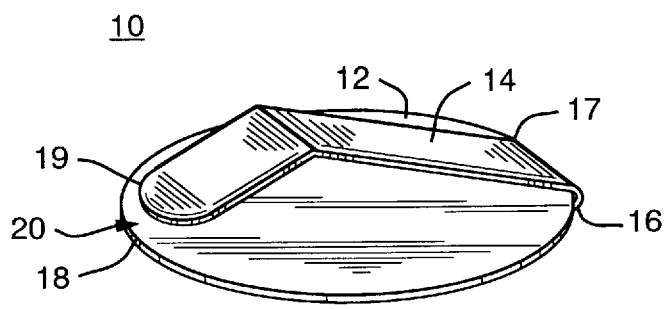
FIG. 1 is a perspective view of the gripping device, according to the present invention.

A gripping device 10, FIG. 1, according to the present invention, is used to grip and possibly remove a relatively small particle attached to or embedded in a larger object. The exemplary application of the present invention is to remove a tick or other parasite from an animal or human, for example, from beneath the fur of a dog, as will be described in greater detail below. The present invention, however, contemplates using the gripping device to grip other relatively small particles from a relatively larger object including, but not limited to, removing stems from fruit, such as strawberries, and slivers or splinters from human skin.

The gripping device 10 includes first and second opposing members 12, 14 coupled together at their proximal ends 16, 17 and spaced apart at distal ends 18, 19 of the first and second opposing members 12, 14. The first opposing member 12 has a larger surface area than the second opposing member 14 so that the gripping device 10 can be more easily held and manipulated by the hand of a user. The distal ends 18, 19 of the first and second opposing members 12, 14 preferably have an arcuate shape to facilitate gripping of the tick or other particle.

Figure 2:
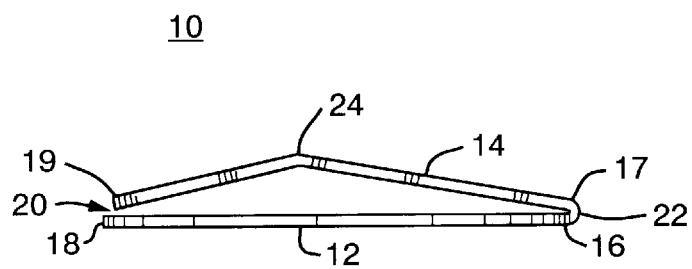
FIG. 2 is a side view of the gripping device, according to the present invention.

An object gripping region 20, FIG. 2, is formed between the distal ends 18, 19 of the first and second opposing members 12, 14. According to the preferred embodiment, the first opposing member 12 is substantially flat. The second opposing member 14 includes a bend 24 such that the distal end 19 of the second opposing member generally faces the distal end 18 of the first opposing member to form the gripping region 20 therebetween. The distal ends 18, 19 of the first and second opposing members 12, 14 are adapted to move together when the first and second opposing members are squeezed by the user such that the gripping region 20 closes against the object or particle. The distal ends 18, 19 are adapted to move apart when the first and second opposing members 12, 14 are released by the user.

The first and second opposing members 12, 14 of the gripping device 10 are preferably formed as one-piece such that an integral hinge 22 is formed between the proximal ends 16, 17 of the first and second opposing members 12, 14. The first and second opposing members 12, 14 are preferably made of a rigid resilient material, such as metal or plastic, such that the integral hinge 22 biases the distal ends 18, 19 to an open position. The distal ends 18, 19 of the first and second opposing members 12,14 are maintained in the open position by the hinge 22 until the first and second opposing members 12, 14 are squeezed by the user.

Figure 3:
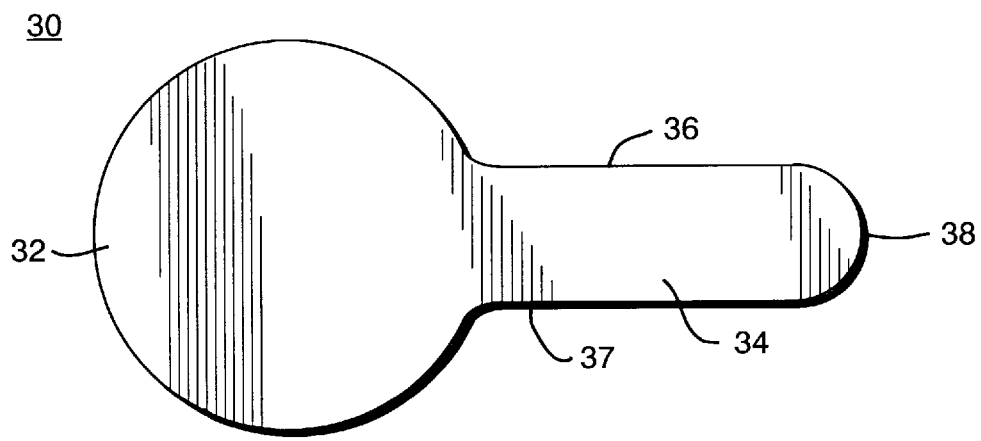
FIG. 3 is a plan view of a piece of material used to make the gripping device, according to the present invention.

In one example, a piece of material 30, FIG. 3, such as aluminum or another similar metal or resilient material, is used to make the gripping device 10. The piece of material 30 includes a first portion 32 having a substantially circular shape and a second portion 34 extending from the first portion 32. The second portion 34 includes substantially parallel edges 36, 37 and an arcuate shaped edge 38 that forms distal end 19. The first and second portions 32, 34 are bent to form the first and second opposing members 12, 14, respectively, as described above. The substantially circular shape of the first opposing member 12 and the arcuate shape of the distal end 19 (FIG. 1) provide a relatively wider gripping region 20 that facilitates the gripping of the relatively small particles.

Figure 4:
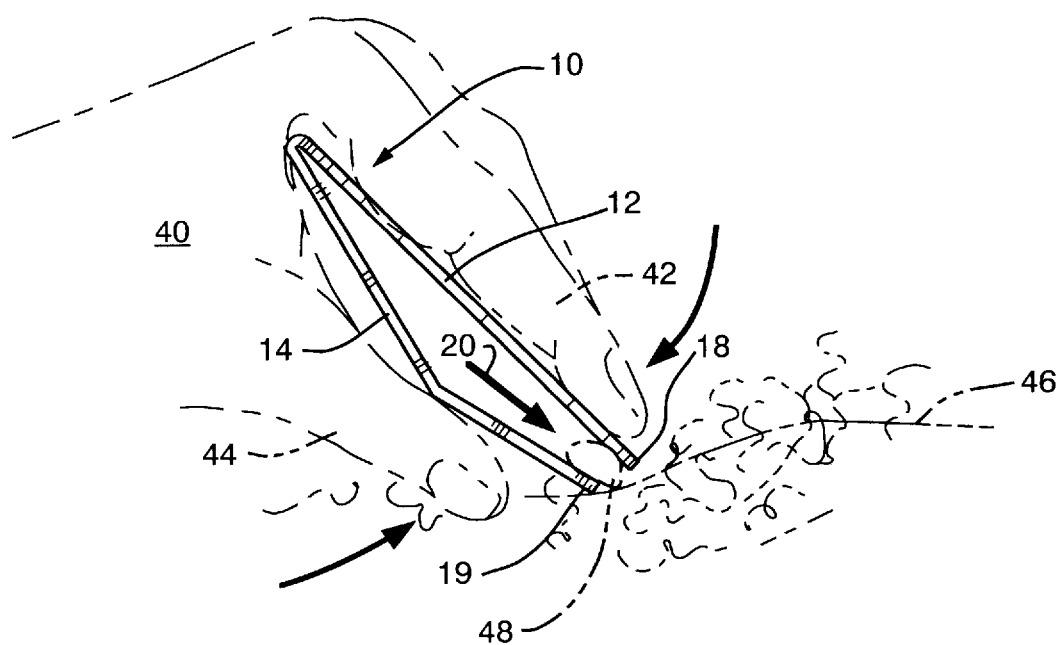
FIG. 4 is a side perspective view of the gripping device, according to the present invention, being used to grip and remove a tick.

In use, a hand 40, FIG. 4, of a user holds the gripping device 10 on either side. For example, the forefingers 42 can be placed on the first opposing member 12 having the relatively larger size while the thumb 44 is placed against the second opposing member 14, or vice versa. The distal ends 18, 19 of the first and second opposing members 12, 14 are placed against the animal 46 such that the tick 48 or other parasite is forced into the gripping region 20 between the distal ends 18, 19 of the first and second opposing members 12, 14. The first and second opposing members 12, 14 are then squeezed together to close the distal ends 18, 19 around the tick 48. After gripping the tick 48 with the gripping device 10, the tick 48 can easily be removed from the animal 46.

Accordingly, the gripping device 10 of the present invention can be more easily held by the user while maneuvering and positioning the gripping device around the relatively small object or particle to be removed. The gripping device of the present invention also has a larger gripping region formed by arcuate shaped ends of the first and second opposing members to facilitate positioning the particle within the gripping region for gripping and removal.

Modifications and substitutions by one of ordinary skill in the art are considered to be within the scope of the present invention which is not to be limited except by the claims which follow.

What is claimed is:

1. A gripping device, for gripping and removing a particle attached to an object, said gripping device comprising:

first and second opposing members coupled together at a proximal end of each of said first and second opposing members and spaced apart at a distal end of each of said first and second opposing members, said first opposing member having a larger surface area than said second opposing member, for facilitating manipulation by a hand of a user; and a gripping region disposed between said distal ends of said first and second opposing members, wherein said second opposing member includes a bend such that said distal end of said second opposing member generally faces said distal end of said first opposing member to form said gripping region therebetween, wherein said distal ends of said first and second opposing members move together when said first and second opposing members are squeezed by said user such that said distal end of said second opposing member contacts said first opposing member proximate said distal end of said first opposing member allowing said gripping region to close against said particle, and wherein said distal ends move apart when said first and second opposing members are released by said user.

2. The gripping device of claim 1 wherein said first opposing member has a substantially circular shape.

3. The gripping device of claim 1 wherein said first opposing member is substantially flat.

4. The gripping device of claim 1 wherein said distal end of said second opposing member has an arcuate shape.

5. The gripping device of claim 4 wherein said second opposing member includes substantially parallel edges extending from said proximal end to said distal end.

6. The gripping device of claim 1 wherein said first and second opposing members are one-piece and form an integral hinge between said proximal ends of said first and second opposing members.

7. The gripping device of claim 6 wherein said first and second opposing members are made of a metal material, wherein said metal material is bent to form said integral hinge at said proximal ends of said first and second opposing members.

8. The gripping device of claim 7 wherein said metal material is aluminum.

9. The gripping device of claim 6 wherein said first and second opposing members are made of a plastic material, wherein said plastic material is bent to form said integral hinge at said proximal ends of said first and second opposing members.

10. A gripping device, for gripping and removing a particle attached to an object, said gripping device comprising:

first and second opposing members coupled together at a proximal end of each of said first and second opposing members, and spaced apart at a distal end of each of said first and second opposing members, wherein said second opposing member is bent such that said distal end of said second opposing member faces said distal end of said first opposing member, and wherein said first opposing member is substantially flat and has a larger surface area than said second opposing member, for being held by a hand of a user;

an integral hinge formed between said proximal ends of said first and second opposing members; and a gripping region disposed proximate said distal ends of said first and second opposing members, wherein each of said distal ends of said first and second opposing members has an arcuate shape, wherein said distal ends of said first and second opposing members move together when said first and second opposing members are squeezed by said user such that said gripping region closes against said particle, and wherein said distal ends move apart when said first and second opposing members are released by said user.

* * * * *